(12) United States Patent
Binder et al.

(10) Patent No.: US 7,303,539 B2
(45) Date of Patent: Dec. 4, 2007

(54) GEL WRAP PROVIDING MUSCULO-SKELETAL SUPPORT

(76) Inventors: David M. Binder, 1928 Hickory Ridge Rd., Richmond, VA (US) 23233; Edward C. Leicht, 443 Camino Laguna Vista, Goleta, CA (US) 93117; William J. Binder, 120 S. Spalding Dr., Suite 340, Beverly Hills, CA (US) 90212

( * ) Notice: Subject to any disclaimer, the term of this patent is extended or adjusted under 35 U.S.C. 154(b) by 307 days.

(21) Appl. No.: 10/334,201

(22) Filed: Dec. 31, 2002

(65) Prior Publication Data

US 2003/0167028 A1 Sep. 4, 2003

Related U.S. Application Data

(63) Continuation-in-part of application No. 09/931,974, filed on Aug. 17, 2001, now Pat. No. 6,963,019.

(60) Provisional application No. 60/226,602, filed on Aug. 21, 2000.

(51) Int. Cl.
*A61F 13/00* (2006.01)

(52) U.S. Cl. .............................. 602/75; 602/48; 602/77

(58) Field of Classification Search ................ 602/41, 602/42, 43, 44, 55, 48, 47; 604/304–308; 128/888, 889, 893, 894; 424/443–449
See application file for complete search history.

(56) References Cited

U.S. PATENT DOCUMENTS

| 4,377,160 A | 3/1983 | Romaine ................. 128/156 |
| 5,540,922 A | 7/1996 | Fabo ....................... 424/402 |
| 5,603,145 A | 2/1997 | Arakawa et al. ............ 24/442 |
| 6,143,946 A * | 11/2000 | Doctor ...................... 602/41 |
| 6,520,926 B2 * | 2/2003 | Hall ........................... 602/64 |

OTHER PUBLICATIONS

Int'l Search Report dated Oct. 29, 2003 for PCT/US03/01287.

* cited by examiner

*Primary Examiner*—Kim M. Lewis
(74) *Attorney, Agent, or Firm*—Drew Wintringham Clifford Chance US LLP (57) ABSTRACT

A multi-layer wrap, and method of use, for providing more comfortable gel treatment to skin and pressure therapy for underlying skin, the wrap allowing for migration of moisture away from the skin while providing compressive musculo-skeletal support to the treatment site.

27 Claims, 6 Drawing Sheets

GEL WRAP PROVIDING MUSCULO-SKELETAL SUPPORT

This application is a continuation-in-part of Ser. No. 09/931,974 filed Aug. 17, 2001, now allowed U.S. Pat. No. 6,963,019, which claims the benefit of Provisional Application 60/226,602 filed Aug. 21, 2000, now abandoned.

BACKGROUND OF THE INVENTION

The present invention relates to a medical or surgical bandage suitable for use in providing musculo-skeletal support and treatment of skin conditions.

Obtaining combined gel treatment and pressure therapy is not easy or convenient under present methods. Typically in the medical and veterinary fields supportive pressure therapy is provided using compression garments or wraps. When used with a gel, a person must typically apply a layer of gel to the area of the body to be treated followed by wrapping another material such as a compression garment or wrap to keep the gel in position. The materials typically used don't provide the elastic support usually desired and therefore often require many turns of the material being wrapped around a body part or many efforts to wrap it properly. Excessive wrapping of a body extremity that includes many turns of a material around the same area will typically apply too much pressure to the wrapped area. Attempting to adjust the pressure exerted by a wrap that requires many turns is difficult and may require completely unwrapping and re-wrapping the area more than once to obtain the desired pressure. Any application of a wrap that exerts too much pressure to the area will often constrict or cut off the vascular circulation to the affected area and may adversely affect the treated area. Furthermore, typical materials lose much of their elasticity after only a couple of uses.

Silicone gel materials are used in the medical field for the management of such conditions, for example, as dermal scarring, varicose veins and stasis ulcers. These silicone materials soften scar tissue and improve the cosmetic appearance of the scar tissue as well as the functional aspects of scars by reducing the constriction of scars and thereby enhancing mobility of the affected body part.

There is a need in the medical and veterinary fields to combine supportive (pressure) therapy with a gel treatment, particularly on the extremities of the body.

SUMMARY OF THE INVENTION

This invention relates to a composite structure which incorporates the pressure therapy features of a firm yet stretchable carrier material with a silicone gel for treatment of skin conditions. In particular, the invention relates to positioning a gel against the skin utilizing a stretchable bandage that also provides the added benefit of orthopedic or musculo-skeletal support for the joint or portion of the body on which the bandage is wrapped.

More specifically, this invention relates to a multi-layered composite material comprising at least a layer of gel bonded to a stretchable carrier layer. In one embodiment, the stretchable carrier may comprise a firm and elastic loop portion of a hook and loop fastener. The stretch carrier layer is useful for positioning the gel layer in place on the body while at the same time providing substantial musculo-skeletal support to the portion of the body around which the bandage is wrapped.

In the case of veterinary applications, fur is used herein interchangeably with skin. Supportive pressure therapy is useful, for example, to provide musculo-skeletal support for joints and muscles, and in the treatment of carpal tunnel syndrome, arthritis, tennis elbow and aiding the musculo-skeletal system and skin in the prevention of injury caused by strenuous exercise and/or athletic activities. Other medical applications for this device may include obstetrical and vascular support.

Obtaining combined gel treatment and pressure therapy is not easy or convenient under present methods. Typically in the medical and veterinary fields supportive pressure therapy is provided using compression garments or wraps. When used with a gel, a person must typically apply a layer of gel to the area of the body to be treated followed by wrapping another material such as a compression garment or wrap to keep the gel in position. The materials typically used don't provide the elastic support usually desired and therefore often require many turns of the material being wrapped around a body part or many efforts to wrap it properly. Excessive wrapping of a body extremity that includes many turns of a material around the same area will typically apply too much pressure to the wrapped area. Attempting to adjust the pressure exerted by a wrap that requires many turns is difficult and may require completely unwrapping and re-wrapping the area more than once to obtain the desired pressure. Any application of a wrap that exerts too much pressure to the area will often constrict or cut off the vascular circulation to the affected area and may adversely affect the treated area. Furthermore, typical materials lose much of their elasticity after only a couple of uses.

Hook and loop fasteners are now commercially available with firm yet stretchable loop portions of various thicknesses and a broad range of elastic properties. The elastic properties provided by the stretchable loop portion make it possible for a bandage using this material to be effectively wrapped as few as one turn around a part of the body while maintaining contact with the skin to be treated. By applying a surface layer of silicone gel to the flat side (non-loop surface) of a stretchable loop portion of a hook and loop fastener, it was discovered that bandages can be produced which provide a surface layer of silicone for uniform skin contact with the added benefit of musculo-skeletal support. The bandage, i.e. wrap, of this invention having a stretchable loop portion as the carrier layer for the gel can therefore follow the many shapes and anatomical contours of the body while at the same time providing secure positioning of the gel on the skin of the user. The characteristics of moisture wicking, which may be provided in the invention through, for example, surface imperfections, in combination with a gel layer and stretch carrier provide greater comfort to the user because the bandage or wrap allows for movement and flexing of the body without reducing effectiveness, i.e. support and resistance to slipping, while keeping the treated area dryer. Thus, the benefits provided by this invention offer the wearer of the bandage greater comfort and durability and makes for the ideal bandage for repeated usage and/or usage over long periods of time. In addition, this invention offers a beneficial combination of advantages for use in exercise and sports activities by simultaneously providing musculo-skeletal support, flexibility, comfort, ease of adjustment, and absorptive properties by absorbing sweat and by providing ventilation and/or moisture wicking to the treatment area.

This invention is an improvement over the prior bandages or wraps in that (a) the carrier material is firm and elastic providing substantial orthopedic support (i.e., musculo-skeletal support) with a limited number of wraps (b) the product is far more durable than materials such as Lycra® and other known, thin elastic based products commonly available, (c)

both pressure and silicone therapies may be applied concomitantly by this invention and therefore eliminating a separate and/or repeated process of fitting more than one material individually, (d) patient compliance may be improved because continued and repeated, even long term, comfortable use of the product is possible without loss of support from the carrier material while in placement and in use, (e) the invention resists slippage, migration and unintended movement while in use, and, (f) the invention does not adhere to the skin nor does it significantly pull hair or fur when it is removed from use. Furthermore, the carrier of the present invention provides the added benefit of a bandage that supplies even pressure to the body across the area being treated. A strip of a complimentary hook portion of the hook and loop fastener provides quick and simple closure of the wrap about the body part while maintaining effective wrap placement even during strenuous activity and/or flexing of the body.

The manufacturing process of this invention lends itself to large-scale production in either flat sheets or long rolls. Final shapes of limitless configurations can then be cut from the sheets or rolls. This provides for rapid and cost effective production of custom-made shapes for any given application or patient.

DETAILED DESCRIPTION OF THE INVENTION

The description provided below references FIGS. 1 through 13 as part of the disclosure and the associated reference numerals.

The device of the present invention, shown in FIGS. 1 through 3, 7 and 8, is generally described as a firm yet stretchable multi-layer bandage with a silicone gel coating 5 on one side. The carrier 10 is a thick, stretchable loop portion of a hook-and-loop fastener such as Velcro®. In a particular embodiment, carrier 10 is about ⅛ inch thick. The silicone gel used in gel 5 is commercially available as either a 1:1, 3:1, or 10:1 mixture of a polydiorganosiloxane resin and a catalyst. Generally speaking, the silicone gel is an addition cured polydimethyl-siloxane gel. This type of gel is well described in the literature, including some of the existing patent literature (e.g. U.S. Pat. No. 4,991,574 ("Pocknell") which is incorporated herein by reference). There is no particular reason to limit our device to silicone gel, if there are other gels that provide clinical benefit. Further, additives may be introduced into the gel, including, for example, oils, Ben-Gay™, and other topical medications and emoluments that seep into the skin area on which the gel is applied. Although other gels may be used, silicone gel has the special benefit of reducing the appearance of hypertrophic and keloid scarring. The advantages of silicone gel are widely known and are also well described in the existing patent literature (e.g. U.S. Pat. Nos. 5,759,560 ("Dilon"), 5,656,279 ("Dillon"), and 5,895,656 ("Hirschowitz et al.") all the contents of which are herein incorporated by reference. Silicone gel is also known to be hydrophobic, so it won't break down or change characteristics in the presence of water or sweat. Cured silicone gel is cohesive (retains its shape) but is not very strong. It can be easily torn, and to be handled by the average person, it must be reinforced with some alternate carrier material.

In the present invention, carrier 10 is preferably a commercially available loop portion of a stretchable hook-and-loop fastener such as, for example Velstretch®. This "stretch" carrier is essentially the traditional loop portion of a hook-and-loop fastener woven with an elastic material. Depending on the degree of "stretch" desired, different elastic interweaves having various elastic properties and thicknesses may be used. For example, carriers which provide a stretch of approximately 50% in one or more directions may be obtained. This carrier, or substrate, provides the backbone, or compressive force, necessary to apply the silicone gel to any contour on the body, especially joints, both large and small, while also providing the benefit of support to the underlying tissue. The physical characteristics of the layers of the wrap allow the gel to stretch with the carrier fabric without the gel cracking or fracturing. The thickness of the carrier also provides support to the joint, so that the pain and discomfort of joint inflammation due to a variety of medical conditions is minimized. An added benefit of the carrier is to provide protection, for example, from abrasion, to the surface of the skin upon which the invention is applied. The support and protective aspects of the present invention, as described above, easily lend themselves to uses on animals as well.

Figure 7:
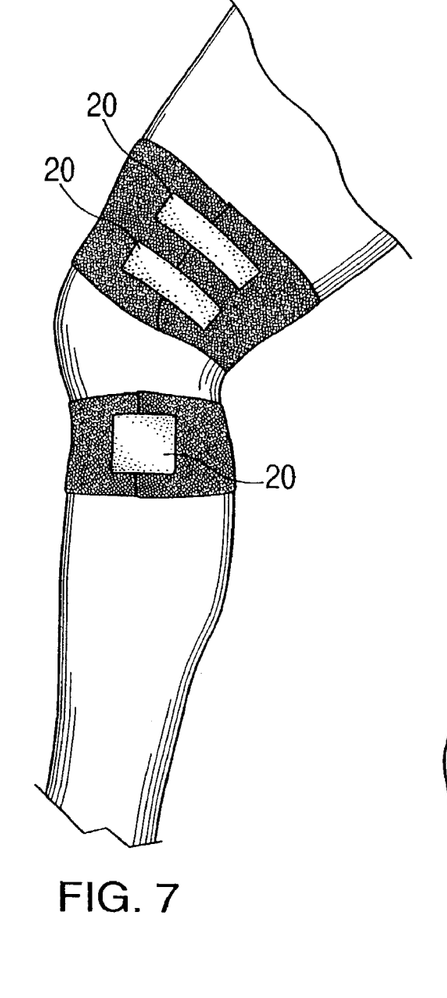
FIG. 7 is a perspective view illustrating the use of particular embodiments of this invention adjacent to the knee joint of a user.
Figure 8:
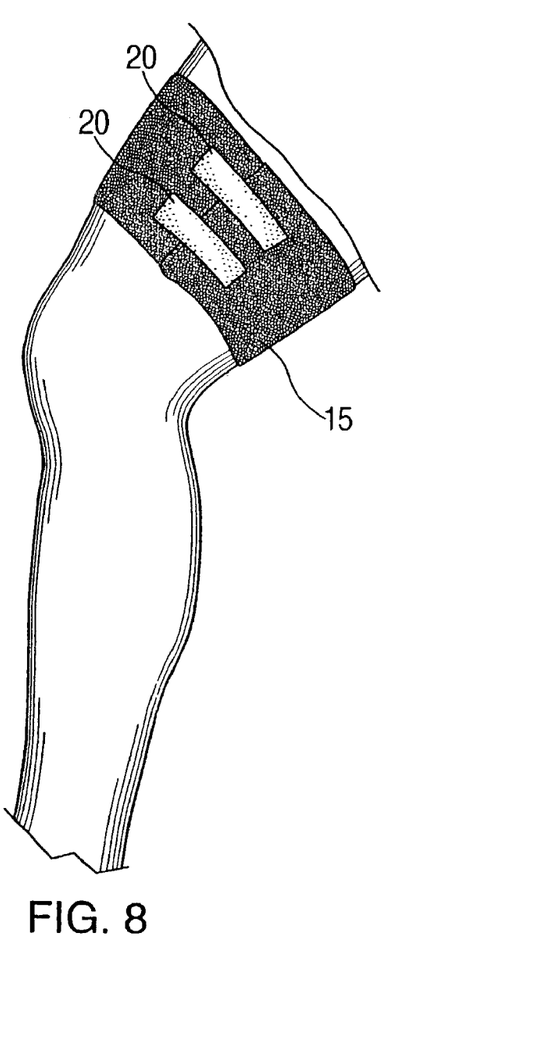
FIG. 8 is a perspective view illustrating the use of an embodiment of the present invention about the thigh of a user, and showing loop surface 15 of the bandage and closure strips 20.

In one embodiment of the present invention, the opposed surface of the "fuzzy" side or "loop" side 15 of the carrier 10 is used as the carrier for the gel. The bandage may be secured about the afflicted joint or area of the body with a complimentary strip of the hook portion 20 (FIG. 4) of a hook and loop fastener material which may be used to keep the bandage closed around the joint or area of the body. Multiple strips or one large strip of width equal to approximately the width of the bandage may also be used to provide proper securing of the bandage as shown in FIG. 7.

In another embodiment, the combined product of this invention has the "loop" side, or loop portion 15 (the soft side), of the stretch carrier 10 on one side and a layer of silicone gel on the other. The gel goes against the skin, and the product is fixed in place by wrapping the body portion with the bandage and applying a complimentary "hook" or closure strip 20 of fastener material at any point along the bandage seam.

Another embodiment of this invention could be provided in a roll form, about 3" wide by about 1 foot long for applications such as those currently employing use of an Ace® type bandage. In this configuration, the present invention can replace the application of Ace-type bandages for musculo-skeletal support and other orthopedic bandages which are specially configured to fit knees, ankles, wrists, elbows, and other problematic joints. Other dimensions applicable to specific applications are also contemplated, such as for use around a thigh or forearm.

For application to areas of the body that require longer lengths to make a wrap, the gel 5 may be applied only to a portion of a length of the carrier material. The gel layer may be provided in a size suitable to treat a desired skin condition only. For example, in the treatment of a scar resulting from a cessarian section operation, the gel portion may be sized only large enough to treat the scar itself, while the carrier 10 is of a length that permits wrapping the bandage around the torso of the person to support the gel in contact with the treatment area.

It is an embodiment of the present invention for the stretchable carrier 10 to provide a platform for the gel to be continuously applied against any existing scar, which will in turn provide the widely understood benefit of reduced scar appearance. Because the gel is deposited on the carrier 10 while the carrier 10 is in the un-stretched position, it should be understood that, as the carrier 10 is expanded, the gel also expands in the same direction. This will allow air to circulate into the treated area, reducing discomfort due to sweating, yet still provide the benefit of the gel applied against the scar. Further, as the carrier 10 is expanded and then closed using the hook section, the carrier 10 provides compression and support to the affected area.

Figure 9:
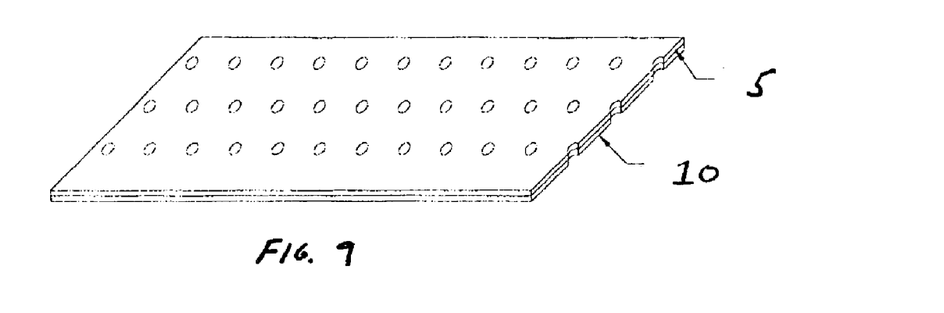
FIG. 9 is an illustration of a perforated embodiment of the present invention.
Figure 10:
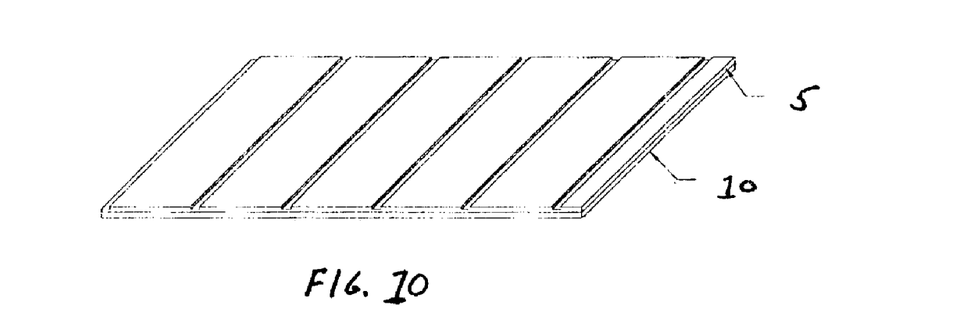
FIG. 10 is an embodiment illustrating gel layer 5 having surface imperfections provided in the form of parallel grooves.
Figure 11:
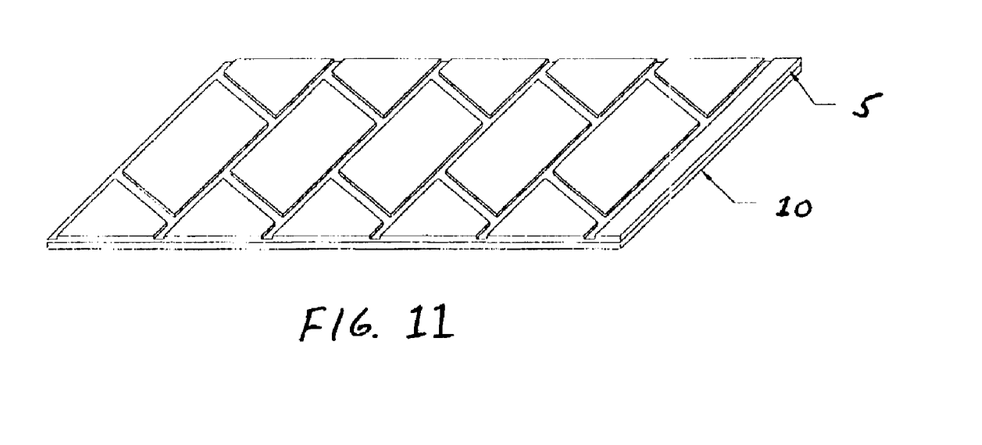
FIG. 11 is an embodiment illustrating gel layer 5 having surface imperfections provided in the form of a tread pattern of intersecting grooves.

In another embodiment, the gel layer may be provided with physical shape characteristics that provide greater comfort to the user. FIG. 9 illustrates a perforated composition. FIGS. 10 and 11 illustrate the gel layer having a series, or tread pattern, of grooves located on the surface of the gel layer that contacts the skin of the user. These surface imperfections, i.e. perforations and/or grooves, aid in directing moisture, such as sweat generated during use of the invention, to the outside of the wrap and away from the skin of the user. They also permit an amount of air to contact the skin within the treatment area. This reduces the amount of sweating in the treatment area caused by bandage use.

In another embodiment of the invention, an absorbent material providing a wicking effect can be incorporated into the composition of the wrap. The wicking material provides greater comfort to the user by wicking moisture, such as sweat, away from the skin of the user. This allows the treated area of the skin to remain dryer during use, and is more comfortable to the user.

The wicking material should be at least as stretchable and flexible as carrier 10 so that the properties of musculo-skeletal support and conformance to bodily contours are not significantly impaired by the incorporation of the wicking material. Polypropylene, cotton and nylon, for example, are some of the many known materials that are suitable for use as a wicking material in this invention.

Figure 12:
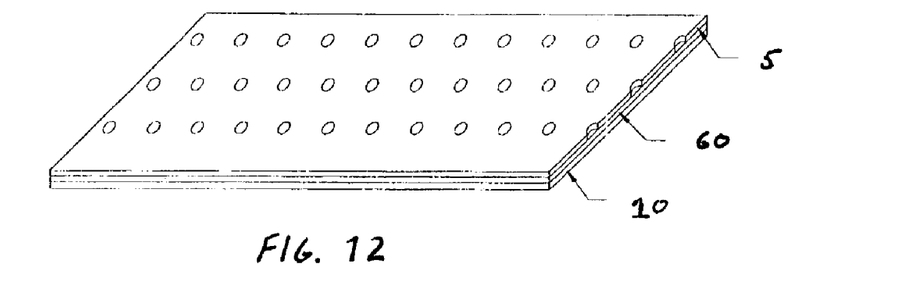
FIG. 12 is an embodiment illustrating a gel layer 5, a wicking layer 60 and a carrier 10.

An embodiment of the present invention combines the musculo-skeletal support and treatment benefits of the gel and carrier composition with the comfort provided by incorporation of a wicking material. In FIG. 12, a layer of wicking material 60 is sandwiched between the carrier 10 and gel 5. In this embodiment, gel layer 5 is perforated to provide greater migration of moisture away from the skin. It is not necessary, however, that the gel layer be perforated for wicking to occur. Moisture will migrate naturally through a solid gel layer. The perforation density, i.e. the number and/or size of perforations in the gel layer, may vary according to the particular requirements of the intended use of the bandage.

Figure 13:
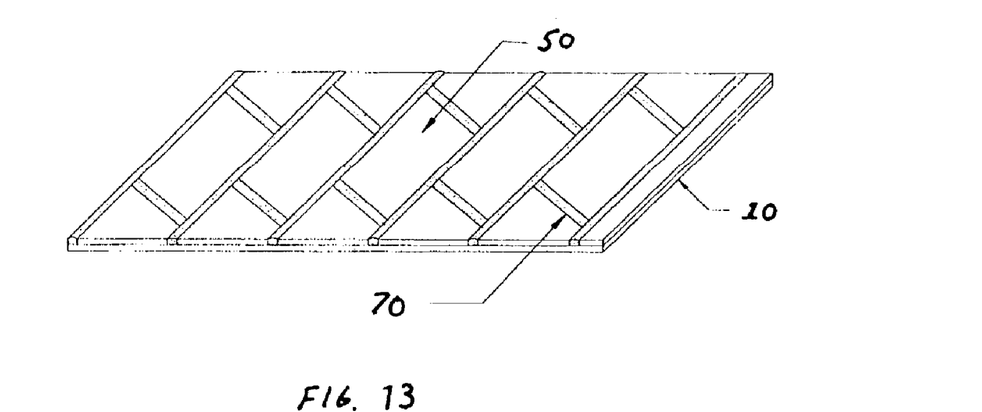
FIG. 13 is an embodiment illustrating gel areas 50, wicking material 70 and carrier 10.

In a preferred embodiment of the invention, referring to FIG. 13, the treatment surface of the bandage, i.e. the surface that is in contact with the skin, is a combination of gel areas 50 and areas of wicking material 70. Each of the gel areas 50 is surrounded by a border of wicking material 70. The structure may be similar to, for example, that of a relatively flattened honey-comb "web" made of wicking material with each of the cells of the "web" containing an amount of gel. The wicking material 70 of this embodiment is in compressed contact with the skin of the treatment area and allows for wicking of moisture away from the treatment area in three dimensions. The particular shape and size of the gel areas and borders of wicking material can vary according to the desired product use.

Referring to FIG. 9, wicking materials of another embodiment of the invention may be used in the manufacture of, and/or incorporated into carrier 10. Moisture that is generated in the treatment area of the skin that migrates through the gel 5 is drawn or wicked away from the gel, and skin, by action of the wicking material in the carrier 10. The wicking action may be increased by the perforation of the gel layer 5 which permits the wicking material of the carrier to more readily absorb moisture from the treatment area because the perforations provide a migration pathway that is less resistant than the solid gel layer.

The silicone gel provides an additional comfort factor of "coolness" against the skin, which is not diminished to any large degree by keeping the present invention in place for the required period. Because the present invention is comfortable, supportive, adaptable, stretchable, trimmable, usable on any joint or area of the body around which it can be wrapped, it is expected to result in higher patient compliance with the treatment.

A method of manufacturing the present invention is shown and described as follows.

The desired gel is mixed as designated by the material manufacturer, i.e. 1:1, 3:1, or 10:1 parts resin and catalyst, although the mixture can be varied to obtain different degrees of tack from the final cured gel. The mixture is poured onto a flat surface, such as large sheet of polycarbonate, and allowed to settle until it is a consistent thickness. The gel, after having been allowed to settle, has a consistent thickness and is surrounded by an appropriate sized wall to contain the gel on the polycarbonate surface. In one embodiment, the gel thickness is approximately 2 mm, although the thickness may vary from as little as 0.5 mm up to 4 mm. Meanwhile, the carrier 10 may be washed in a mild soapy solution such as Ivory® soap to remove the oils and agents used in processing the fabric, and allowed to air dry. After the gel is settled to a consistent thickness (about 20–60 minutes) the dry carrier 10 is placed on top with the loop surface of the carrier 10 away from the gel. The assembled materials are then allowed to cure. In a preferred embodiment, the combined gel and carrier 10 are placed in a curing oven for 1–3 hours and at a temperature of about 100 to 180 degrees centigrade until the gel is cured. The specific time and temperature of the curing process can be determined based on the type of gel composition and the desired cured properties of the bandage. The appropriate curing temperature and curing time can then be varied accordingly. The cured, assembled materials are then removed from the oven and can then be cut into any shape desired.

Figure 1:
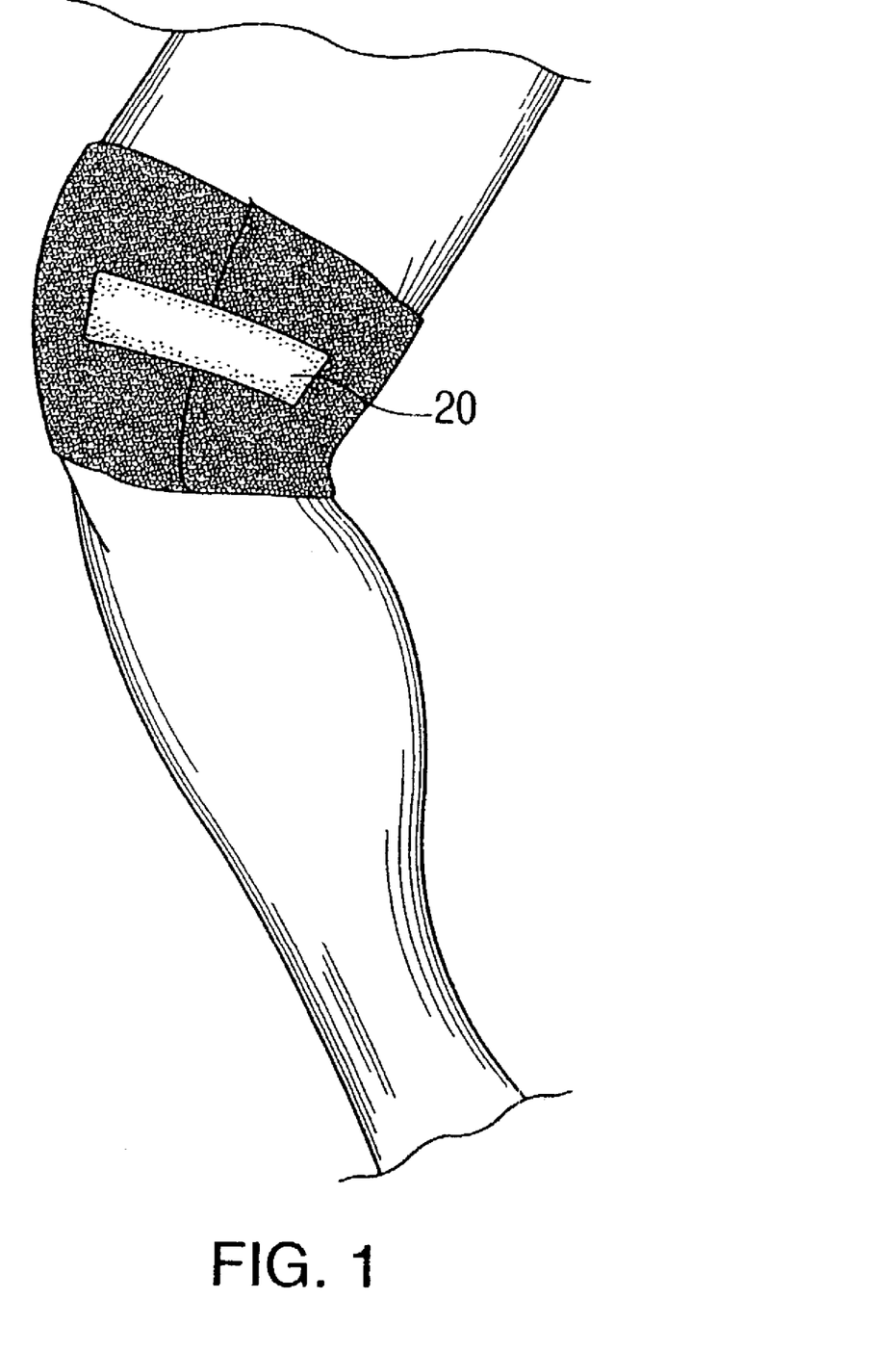
FIG. 1 is a perspective view illustrating the use of one embodiment of this invention on the knee of a user.
Figure 2:
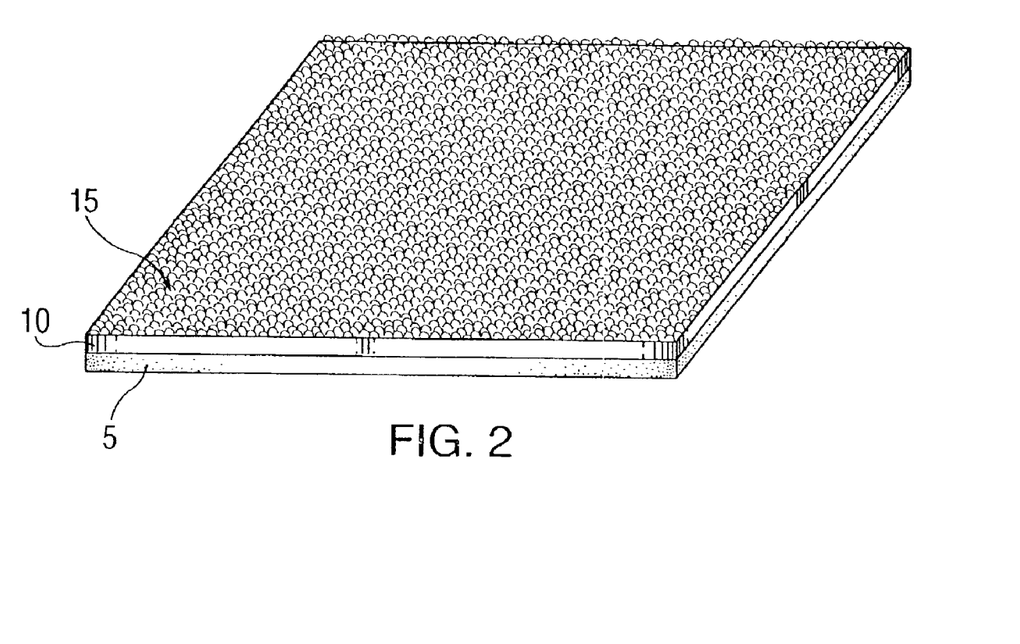
FIG. 2 is an embodiment illustrating gel layer 5 bonded to carrier 10 having loop surface 15.
Figure 3:
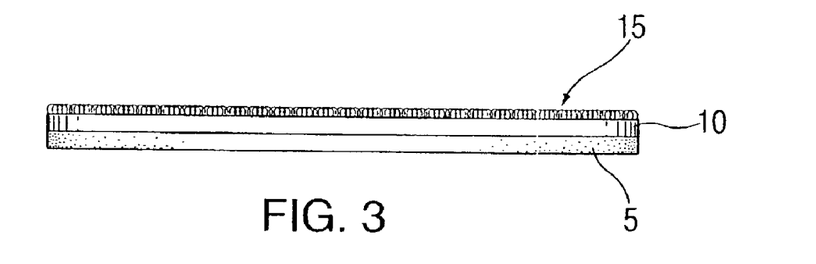
FIG. 3 illustrates carrier 10, having a loop surface 15, bonded to gel layer 5.
Figure 4:
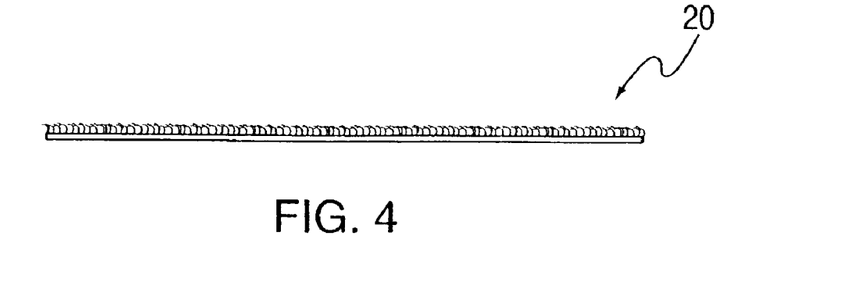
FIG. 4 illustrates closure strip 20
Figure 5:
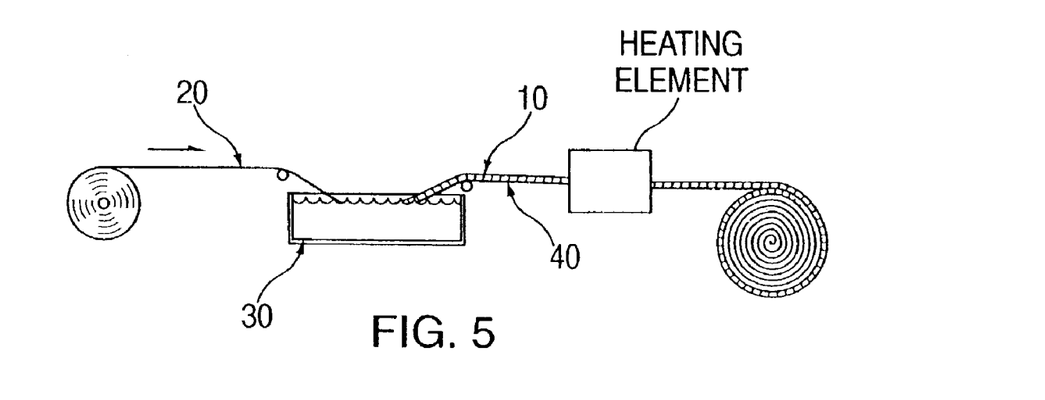
FIG. 5 illustrates a method of manufacture using gel bath 30 and carrier 10.

The present invention also lends itself well to mass production by coextrusion as shown in FIG. 5. In this embodiment, stretchable carrier 10 is continuously unrolled from a large roll of material onto a bath 30 of gel. As the carrier 10 is removed from the bath 30 a layer of gel 40 adheres to the carrier 10 and settles to a uniform thickness. The stream of combined carrier/gel is then passed through a heating oven and cured. At the other end of the oven are take-up rolls and/or cutting fixtures to facilitate rolling or cutting the cured product into any desired configuration.

Figure 6:
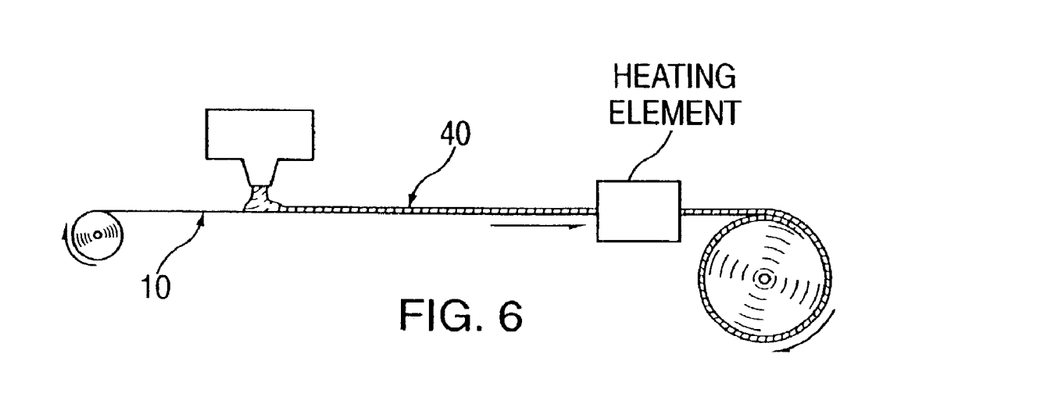
FIG. 6 illustrates river of carrier 10 and uncured gel compound 40.

In another embodiment shown in FIG. 6, an amount of gel 40 is deposited onto a river of carrier 10 as the carrier 10 passes beneath the gel. A layer of gel is formed on the side of the carrier 10 opposite the loops and the gel is allowed to settle to a uniform thickness. The river of combined carrier/gel material is then passed through a heating oven and cured. At the other end of the oven are take-up rolls and/or cutting fixtures to facilitate rolling or cutting the cured product into any desired configuration.

Using either of the previous embodiments, there are specific production techniques which will result in a consistent layer of gel being applied to the flat side of the stretch carrier 10, opposite the loop side.

What is claimed is:

1. A multi-layer wrap comprising:
   a silicone gel layer having a skin-contacting surface and an opposite surface, wherein the skin-contacting surface contains surface imperfections which allow moisture to migrate away from the skin surface;
   an elastic and supportive carrier layer having an outer loop surface and an opposite surface, wherein the carrier layer is the stretchable loop portion of a hook and loop fastener and wherein a moisture wicking material is incorporated into the composition of the carrier layer; and
   wherein the opposite surface of the carrier layer is bonded to the opposite surface of the gel layer to form a two-ply composite.

2. The wrap according to claim 1, wherein the silicone gel layer is perforated.

3. The wrap according to claim 1, wherein the wicking material is selected from the group consisting of cotton, nylon, and polypropylene.

4. The wrap according to claim 1, wherein the wicking material is selected from the group consisting of cotton, nylon, polypropylene.

5. The wrap according to claim 1, further comprising a closure strip for removably securing the wrap around a part of a body, wherein the closure strip is the hook portion of a hook and loop fastener.

6. A method of providing skin treatment and musculo-skeletal support comprising:
   wrapping a bandage around a portion of the body to be treated, said bandage having a gel layer having surface imperfections provided on a skin contacting surface and a carrier layer bonded to an opposing surface of said gel layer, said carrier being both firm and elastic;
   stretching said bandage around said portion of the body;
   securing said bandage in a closed position; and,
   migrating moisture through the surface imperfections and away from the portion of the body being treated.

7. The method of claim 6; wherein, said surface imperfections are grooves.

8. The method of claim 6; wherein, said surface imperfections are penetrations.

9. A method of providing skin treatment and musculo-skeletal support comprising:
   wrapping a bandage around a portion of the body to be treated, said bandage having a gel layer having a gel layer for contacting the skin of the body portion to be treated, a moisture wicking material, and a carrier bonded to said gel and said wicking material, said carrier being both rigid and elastic;
   stretching said bandage around said portion of the body;
   securing said bandage in a closed position; and,
   wicking moisture away from the portion of the body being treated.

10. A multi-layer wrap comprising:
    a silicone gel layer having a skin-contacting surface and an opposite surface, wherein the skin-contacting surface contains surface imperfections which allow moisture to migrate away from the skin surface;
    an elastic and supportive carrier layer having an outer loop surface and an opposite surface, wherein the carrier layer is the stretchable loop portion of a hook and loop fastener; and
    wherein the opposite surface of the carrier layer is bonded to the opposite surface of the gel layer to form a two-ply composite.

11. The wrap of claim 10, wherein the surface imperfections are grooves.

12. The wrap of claim 10, wherein the surface imperfections are penetrations through the gel layer.

13. The wrap according to claim 10, wherein the carrier provides compressive, musculo-skeletal support in the area of application to a wearer of the wrap.

14. The wrap according to claim 13, wherein the carrier has an elastic modulus of about 50%.

15. The wrap according to claim 10, wherein the silicone gel contains medical additives.

16. The wrap according to claim 10, further comprising a closure strip for removably securing the wrap around a part of a body, wherein the closure strip is the hook portion of a hook and loop fastener.

17. A multi-layer wrap comprising:
    an inner layer of a silicone gel having a skin-contacting surface and an opposite surface;
    an outer layer of an elastic and supportive carrier having an outer loop surface and an opposite surface, wherein the carrier is the stretchable loop portion of a hook and loop fastener;
    a layer of a moisture wicking material sandwiched between the opposite surface of the gel layer and the opposite surface of the carrier layer; and
    wherein the layers are bonded together to form a three-ply composite.

18. The wrap according to claim 17, wherein the wicking material is selected from the group consisting of cotton, nylon, and polypropylene.

19. The wrap according to claim 17, wherein the carrier provides compressive, musculo-skeletal support in the area of application to a wearer of the wrap.

20. The wrap according to claim 19, wherein the carrier has an elastic modulus of about 50%.

21. The wrap according to claim 17, wherein the silicone gel contains medical additives.

22. A multi-layer wrap comprising:
    an inner layer of silicone gel areas surrounded by a wicking material, which layer has a skin-contacting surface and an opposite surface; and
    an outer layer of an elastic and supportive carrier having an outer loop surface and an opposite surface, wherein the carrier is the stretchable loop portion of a hook and loop fastener; and
    wherein the opposite surface of the inner layer is bonded to the opposite surface of the carrier layer to form a two-ply composite.

23. The wrap according to claim 22, wherein the inner layer consists of a flattened, honey-combed cellular web wherein the cells contain the silicone gel.

24. The wrap according to claim 22, wherein the carrier provides compressive, musculo-skeletal support in the area of application to a wearer of the wrap.

25. The wrap according to claim 24, wherein the carrier has an elastic modulus of about 50%.

26. The wrap according to claim 22, wherein the silicone gel contains medical additives.

27. The wrap according to claim 24, further comprising a closure strip for removably securing the wrap around a part of a body, wherein the closure strip is the hook portion of a hook and loop fastener.

* * * * *